United States Patent
Wu et al.

(10) Patent No.: US 10,347,031 B2
(45) Date of Patent: Jul. 9, 2019

(54) APPARATUS AND METHOD OF TEXTURE MAPPING FOR DENTAL 3D SCANNER

(71) Applicant: Carestream Dental Technology Topco Limited, London (GB)

(72) Inventors: Yingqian Wu, Shanghai (CN); Victor C. Wong, Pittsford, NY (US); Qinran Chen, Shanghai (CN); Zhaohua Liu, Shanghai (CN)

(73) Assignee: Carestream Dental Technology Topco Limited, London (GB)

( * ) Notice: Subject to any disclaimer, the term of this patent is extended or adjusted under 35 U.S.C. 154(b) by 0 days.

(21) Appl. No.: 15/546,396

(22) PCT Filed: Sep. 11, 2015

(86) PCT No.: PCT/US2015/049627
§ 371 (c)(1),
(2) Date: Jul. 26, 2017

(87) PCT Pub. No.: WO2016/144382
PCT Pub. Date: Sep. 15, 2016

(65) Prior Publication Data
US 2018/0025529 A1    Jan. 25, 2018

Related U.S. Application Data

(60) Provisional application No. 62/130,110, filed on Mar. 9, 2015.

(51) Int. Cl.
*G06T 15/04* (2011.01)
*A61B 5/00* (2006.01)
(Continued)

(52) U.S. Cl.
CPC ............ *G06T 15/04* (2013.01); *A61B 5/0088* (2013.01); *A61B 5/1077* (2013.01); *G01J 3/501* (2013.01); *G01J 3/508* (2013.01); *G06T 2210/41* (2013.01)

(58) Field of Classification Search
None
See application file for complete search history.

(56) References Cited

FOREIGN PATENT DOCUMENTS

| EP | 0837659 | 7/1996 |
|----|---------|--------|
| EP | 1607041 | 6/2005 |
| EP | 2786722 | 3/2014 |

OTHER PUBLICATIONS

International Search Report, International application No. PCT/US2015/049627, dated Dec. 18, 2015, 3 Pages.
(Continued)

*Primary Examiner* — Nicholas R Wilson

(57) ABSTRACT

A method for color texture imaging of teeth with a monochrome sensor array obtains a 3-D mesh representing a surface contour image according to image data from views of the teeth. For each view, recording image data generates sets of at least three monochromatic shading images. Each set of the monochromatic shading images is combined to generate 2-D color shading images, corresponding to one of the views. Each polygonal surface in the mesh is assigned to one of a subset of the views. Polygonal surfaces assigned to the same view are grouped into a texture fragment. Image coordinates for the 3-D mesh surfaces in each texture fragment are determined from projection of vertices onto the view associated with the texture fragment. The 3-D mesh is rendered with texture values in the 2-D color shading images corresponding to each texture fragment to generate a color texture surface contour image.

20 Claims, 20 Drawing Sheets

(51) Int. Cl.
*G01J 3/50* (2006.01)
*A61B 5/107* (2006.01)

(56) References Cited

OTHER PUBLICATIONS

C. Frueh et al., Automated Texture Mapping of 3D City Models With Oblique Aerial Imagery, Proceedings of the 2$^{nd}$ International Symposium on 3D Data Processing, Visualization, and Transmission, 9 pages.

Wolfgang Niem et al., Mapping Texture from Multiple Camera Views Onto 3D-Object Models for Computer Animation, XP-002347355, 1995, 7 Pages.

Wolfgang Niem, Automatic reconstruction of 3D objects using a mobile camera, Imaging and Vision Computing, vol. 17, No. 2, XP-002258790, Feb. 1999, ISSN: 0262-8856, pp. 125-134.

C. Rocchini et al., Multiple Textures Stitching and Blending on 3D Objects, Eurographics Rendering Workshop, Dec. 1999, XP-055064409, 13 Pages.

H. Lensch et al., Automated Texture Registration and Stitching for Real World Models, Computer Graphics and Applications, 2000, XP-010523024, pp. 317-452.

APPARATUS AND METHOD OF TEXTURE MAPPING FOR DENTAL 3D SCANNER

CROSS REFERENCE TO RELATED APPLICATIONS

This application claims the benefit of and is a U.S. National Phase filing of PCT Application PCT/US2015/049627 filed Sep. 11, 2015 entitled "APPARATUS AND METHOD OF TEXTURE MAPPING FOR DENTAL 3D SCANNER", in the name of Yingqian Wu et al, which claims benefit of U.S. Provisional application U.S. Ser. No. 62/130,110, provisional filed on Mar. 9, 2015, entitled "APPARATUS AND METHOD OF TEXTURE MAPPING FOR DENTAL 3D SCANNER", in the name of Yingqian Wu, all of which are incorporated herein by reference in their entirety.

FIELD OF THE INVENTION

The invention relates generally to the field of surface shape imaging and more particularly relates to surface imaging and display of 3-D color images in intraoral applications.

BACKGROUND

Surface contour information can be particularly useful for assessment of tooth condition and is helpful for various types of dental procedures, such as for restorative dentistry. A number of techniques have been developed for obtaining surface contour information from various types of objects in medical, industrial, and other applications. Optical 3-dimensional (3-D) measurement methods provide shape and depth information using light directed onto a surface in various ways. Among types of imaging methods used for contour imaging are those that generate a series of light patterns and use focus or triangulation to detect changes in surface shape over the illuminated area.

Fringe projection imaging uses patterned or structured light and triangulation to obtain surface contour information for structures of various types. In fringe projection imaging, a pattern of lines is projected toward the surface of an object from a given angle. The projected pattern from the surface is then viewed from another angle as a contour image, taking advantage of triangulation in order to analyze surface information based on the appearance of contour lines. Phase shifting, in which the projected pattern is incrementally shifted spatially for obtaining additional measurements at the new locations, is typically applied as part of fringe projection imaging, used in order to complete the contour mapping of the surface and to increase overall resolution in the contour image.

Color sensor arrays are more costly and complex than monochrome sensor arrays. In addition, sensor arrays that generate RGB data directly are inherently less efficient and less sensitive to low light level conditions, such as those common in intra-oral imaging.

In spite of cost, it can be appreciated that there would be value in providing 3-D surface contour images in color for both diagnostic and aesthetic purposes. Known approaches to this imaging problem provide ways to associate color to areas of the volume image. However, these approaches fall short of what is needed for providing color volume images that faithfully reproduce color texture. In general, texture of a surface relates to detailed surface structure and, in an imaging context, provides a more accurate representation of how light is reflected from the surface. Color texture also includes the spatial arrangement and intensity of color in the image. Attributes of color texture can be based on the directional distribution of reflected or transmitted light, typically described by attributes like glossy, shiny versus dull, matte, clear, turbid, distinct, or related to microsurface structure, such as roughness or smoothness, shading, and other attributes. Color texture representation is related to improved definition of edges, for example, and allows features within the mouth, and of the anatomy more generally, to be more clearly visualized.

Among proposed solutions for providing a measure of color information for 3-D images is that described, for example, in patent disclosure EP 0837659 entitled "Process and Device for Computer-Assisted Restoration of Teeth" to Franetzki, that obtains color data in a conventional manner using a color detector and then superimposes the 2-D Red (R), Green (G), and Blue (B) or RGB color image onto the 3-D volume image when it is displayed. This type of simulated color solution, however, does not provide true 3-D color image data. Provided that it can be correctly scaled and registered to the volume image data when overlaid onto the 3-D surface image, the simultaneously displayed and superimposed color content as described in EP 0837659, would be accurate at a single viewing angle only. Any other view of the 3-D surface would not have the superimposed color image content.

Thus, it can be appreciated that there is a need for an image processing method that provides 3-D image data of the teeth showing color as well as color texture content, using a single image capture apparatus that employs a monochrome sensor array.

SUMMARY

It is an object of this application to advance the art of surface contour detection of teeth and related intraoral structures.

Method and/or apparatus embodiments of this application can address the need for improved representation of color texture that relates to the volume image acquired from a patient.

Another aspect of this application is to address, in whole or in part, at least the foregoing and other deficiencies in the related art.

It is another aspect of this application to provide, in whole or in part, at least the advantages described herein.

These aspects are given only by way of illustrative example, and such objects may be exemplary of one or more method and/or apparatus embodiments of the invention. Other desirable objectives and advantages inherently achieved by the disclosed invention may occur or become apparent to those skilled in the art. The invention is defined by the appended claims.

According to one aspect of the invention, there is provided a method for forming color texture mapping to a 3-D contour image of one or more teeth in an intra-oral camera with a monochrome sensor array, that can include obtaining a 3-D mesh representing a 3-D surface contour image of the one or more teeth according to image data recorded from a plurality of views of the one or more teeth, wherein for each of the plurality of views, recording image data comprises generating a plurality of sets of at least three monochromatic shading images by projecting light of at least three different spectral bands onto the one or more teeth and recording the corresponding image data on the monochrome sensor array; combining each set of the at least three monochromatic shading images to generate a plurality of 2-D color shading images, where each of the plurality of 2-D color shading images corresponds to one of the plurality of views; assigning each polygonal surface in the 3-D mesh representing the 3-D surface contour image of the one or more teeth to one of a subset of the plurality of views; grouping 3-D mesh polygonal surfaces assigned to the same view into a texture fragment; determining image coordinates for vertices of the 3-D mesh polygonal surfaces in each texture fragment from projection of the vertices onto the view associated with the texture fragment; and rendering the 3-D mesh with texture values in the 2-D color shading images corresponding to each texture fragment according to the determined image coordinates to generate a color texture 3-D surface contour image of the one or more teeth.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting system optics, for example, are not shown in the drawings in order to simplify description.

DESCRIPTION OF EXEMPLARY EMBODIMENTS

Figure 1:
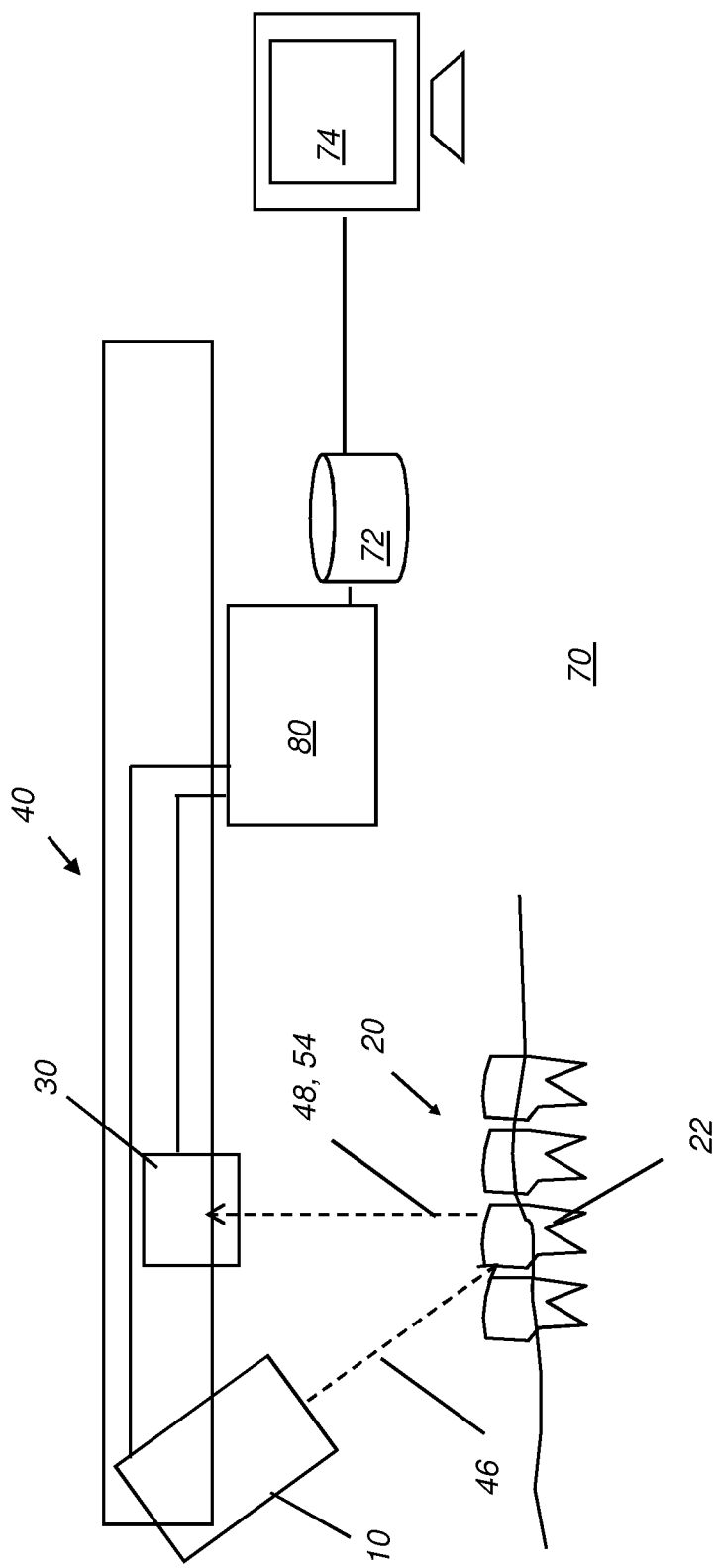
FIG. 1 is a schematic diagram showing an imaging apparatus for obtaining color 3-D information from a patient's teeth.

This application claims the benefit of U.S. Provisional application U.S. Ser. No. 62/130,110, provisionally filed on Mar. 9, 2015, entitled "AN APPARATUS AND METHOD OF TEXTURE MAPPING FOR DENTAL 3D SCANNER" in the names of Yingqian Wu et al., which is incorporated herein by reference in its entirety.

The following is a detailed description of the exemplary embodiments of the invention, reference being made to the drawings in which the same reference numerals identify the same elements of structure in each of the several figures.

In the context of the present disclosure, the terms "spectral band" or "wavelength band" indicate a defined, continuous range of wavelengths for illumination and imaging and are used interchangeably with the term "color". For example, the phrase "red spectral band" is used to indicate visible light that is generally within the red wavelength range that extends continuously from about 620 nm to about 700 nm. In an imaging context, light of two spectral bands are considered to be substantially non-overlapping when there is no visually perceptible crosstalk between bands.

In the context of the present disclosure, the term "color component image", equivalent to data in a single color plane, refers to the image data that is acquired using an image captured with light of a single spectral band. Thus, for example, a conventional full-color RGB image is formed from red, green, and blue components, wherein each individual image is termed a color component image.

The term "set", as used herein, refers to a non-empty set, as the concept of a collection of elements or members of a set is widely understood in elementary mathematics. The term "subset", unless otherwise explicitly stated, is used herein to refer to a non-empty proper subset, that is, to a subset of the larger set, having one or more members. For a set S, a subset may comprise the complete set S. A "proper subset" of set S, however, is strictly contained in set S and excludes at least one member of set S.

An "ordered set" has its conventional meaning as used in set theory, relating to a set whose elements have a non-ambiguous ordering, such as the set of natural numbers that are ordered in an ascending sequence, for example.

The schematic diagram of FIG. 1 shows an imaging apparatus 70 for combined volume and color imaging of the teeth. For volume imaging, a camera 40 projects structured imaging patterns 46 onto surface 20 of teeth 22 to obtain a contour image 48 according to an exemplary embodiment of the application. A control logic processor 80 or other type of computer controls the operation of an illumination array 10 and acquires digital image data obtained from a monochrome imaging sensor array 30. During volume imaging, illumination array 10 projects patterned light onto an area 54 of the tooth, typically including structured patterns with multiple lines of light (e.g., having a predetermined spacing between lines). Image data from surface 20 is obtained from the patterned light detected by imaging sensor array 30. Control logic processor 80 processes the received image data and stores the mapping in memory 72. The reconstructed 3-D surface image from memory 72 is then optionally displayed on a display 74. Memory 72 may also include a display buffer.

Figure 2:
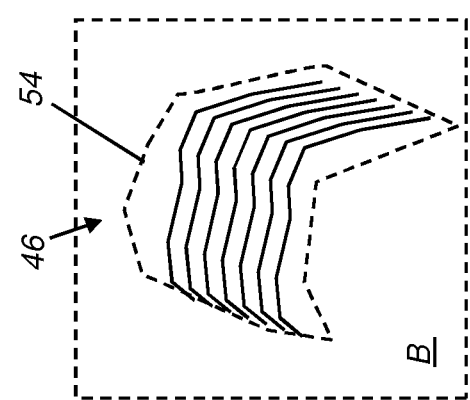
FIG. 2 is a schematic diagram that shows projection of a structured pattern onto the surface of a tooth.
Figure 2:
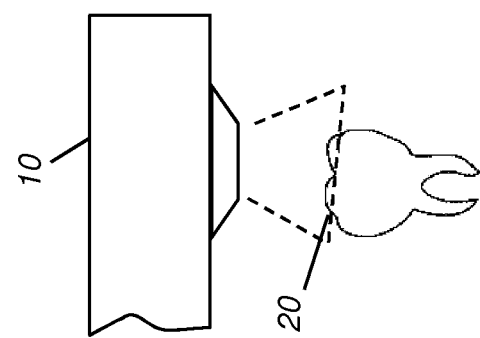

The schematic view of FIG. 2 shows, in an inset labeled B, a portion of a typical fringe pattern 46 that is directed onto area 54 of surface 20 from illumination array 10. The structured pattern that is projected can be at the same power level at each shifted position. Alternately, different power levels can be used for projecting the structured pattern.

According to some exemplary embodiments for color contour imaging, camera 40 is used in still mode, held in the same fixed position for obtaining color component images as that used for structured light pattern projection and imaging. In other exemplary embodiments, for color contour imaging, camera 40 can move while obtaining color component images and/or can move when used for structured light pattern projection and imaging.

Illumination array 10 projects light of different color component wavelengths, typically Red (R), Green (G), and Blue (B), one at a time, and captures a separate image on monochrome sensor array 30 at each wavelength band. However, other color component combinations can be used. The captured images are also processed and stored by control logic processor 80 (FIG. 1).

Figure 3:
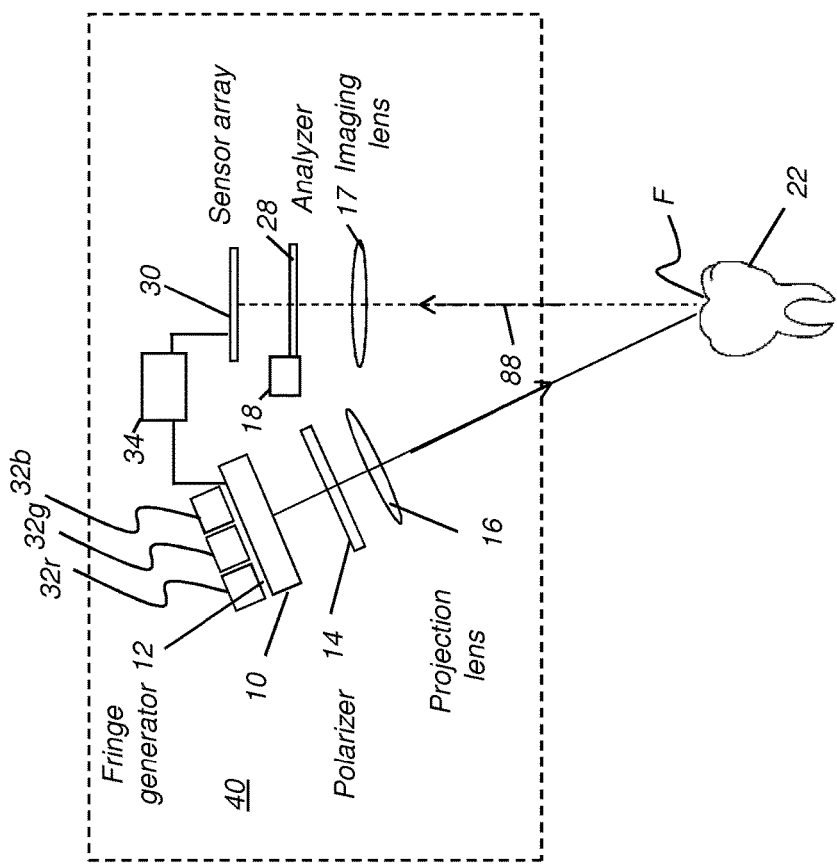
FIG. 3 is a schematic diagram showing components of a camera for intra-oral imaging that obtains a color surface contour image of a tooth using a monochrome sensor array.

The schematic diagram of FIG. 3 shows internal components of camera 40 for obtaining 3-D surface contour and color data according to an exemplary embodiment of the application. A fringe pattern generator 12 is energizable to form the structured light from illumination array 10 as a type of structured illumination or fringe pattern illumination, and to project the structured light thus formed as incident light toward tooth 22 through an optional polarizer 14 and through a projection lens 16. Light reflected and scattered from tooth 22 can be provided to sensor array 30 through imaging optics (e.g., an imaging lens 17 and an optional analyzer 28). Sensor array 30 is disposed along a detection path 88, at the image plane of imaging lens 17. A processor 34 in camera 40 accepts image content and other feedback information from sensor array 30 and, in response to this and other data, is actuable to effect the operation of pattern generator 12, as described in more detail subsequently.

One function of processor 34 for fringe projection imaging is to incrementally shift the position of the fringe and trigger the sensor array 30 to take images that are then used to calculate three-dimensional information of the tooth surface. For the phase-shifting fringe projection method, at least three images are typically needed in order to provide enough information for calculating the three-dimensional information of the object. Where only three fringe images are obtained, the relative positions of the fringes for each of these three projected images are typically shifted by one-third or other fraction of the fringe period. Processor 34 can be a computer, microprocessor, or other dedicated logic processing apparatus that executes programmed instructions and is in communication with control logic processor 80 that provides imaging system functions as described previously with respect to FIG. 1.

Intra-oral camera 40 of FIG. 3 optionally uses polarized light for surface contour imaging of tooth 22. Polarizer 14 provides the fringe pattern illumination from fringe pattern generator 12 as linearly polarized light. In one embodiment, the transmission axis of analyzer 28 is parallel to the transmission axis of polarizer 14. With this arrangement, only light with the same polarization as the fringe pattern is provided to the sensor array 30. In another embodiment, analyzer 28, in the path of reflected light to sensor array 30, can be rotated by an actuator 18 into either an orientation that matches the polarization transmission axis of polarizer 14 and obtains specular light from surface portions of the tooth or an orientation orthogonal to the polarization transmission axis of polarizer 14 for reduced specular content, obtaining more of the scattered light from inner portions of the tooth. In certain exemplary embodiments herein, combinations of polarized and non-polarized light can be used.

Also shown in FIG. 3 is a red light source 32r, a green light source 32g, and a blue light source 32b for providing color light for capturing three grayscale images, also called monochromatic shading images needed for construction of a full color image. Each of these light sources can include a single light emitting element, such as a light-emitting diode (LED) or of multiple light emitting elements. In the embodiment shown, the illumination path for structured pattern light from the fringe generator and the RGB light is the same; the detection path of light toward sensor array 30 is also the same for both structured pattern and RGB image content. Camera 40 has a focal point or focal plane F.

Figure 4A:
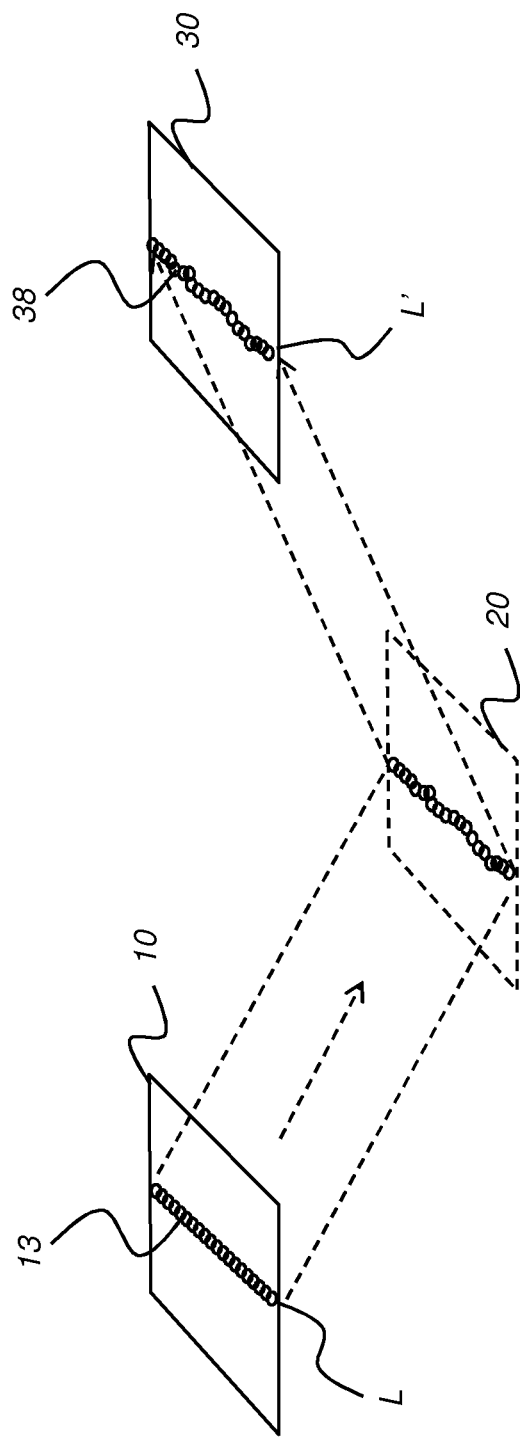
FIG. 4A is a schematic diagram that shows how patterned light is used for obtaining surface contour information.

The schematic diagram of FIG. 4A shows, with the example of a single line of light L, how patterned light from pattern generator 12 is used for obtaining surface contour information. A mapping is obtained as illumination array 10 directs a pattern of light onto surface 20 and a corresponding image of a line L' is formed on an imaging sensor array 30. Each pixel 38 of the projected pattern on imaging sensor array 30 maps to a corresponding pixel 13 on illumination array 10 according to modulation by surface 20. Shifts in pixel position, as represented in FIG. 4A, yield useful information about the contour of surface 20. It can be appreciated that the basic pattern shown in FIG. 4A can be implemented in a number of ways, using a variety of illumination sources and sequences and using one or more different types of sensor arrays 30.

Figure 4B:
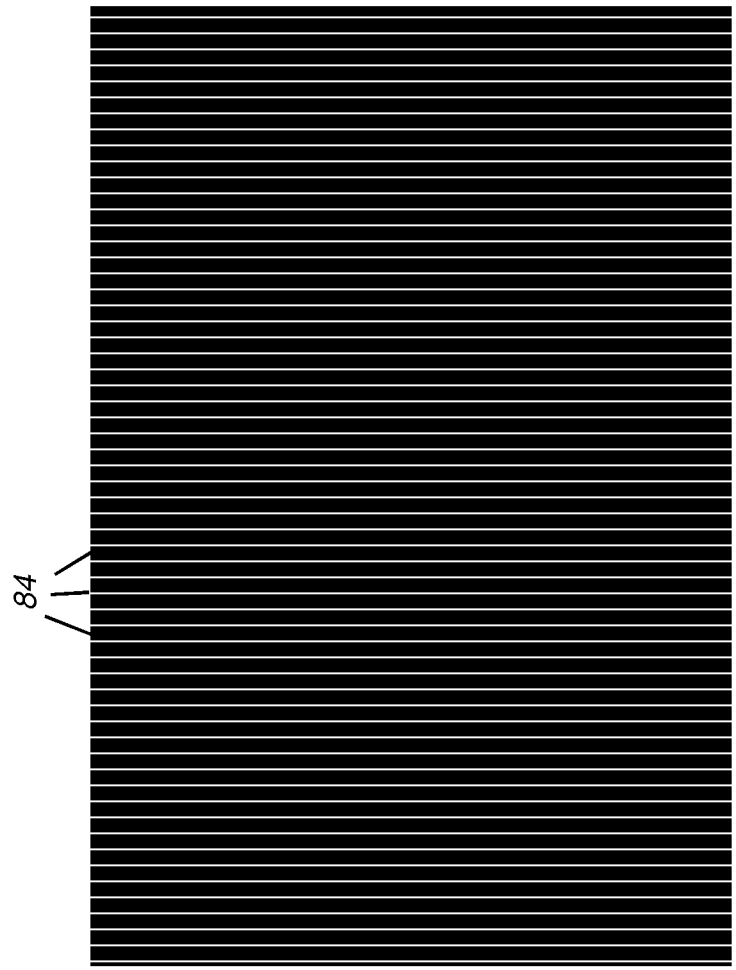
FIG. 4B is a plan view of one structured light pattern having multiple lines of light spaced apart from each other.

The plan view of FIG. 4B shows one structured light pattern 56 having multiple lines of light 84 spaced apart from each other. According to an exemplary embodiment of the application, pattern 56 is directed to the tooth surface in a sequence or series of projected images in which lines 84 are incrementally shifted to the right or, alternately, to the left, in successive images of the projected series.

Illumination array 10 (FIG. 3) can utilize any of a number of types of arrays used for light modulation and light patterning, such as a liquid crystal array or digital micro-mirror array, such as that provided using the Digital Light Processor or DLP device from Texas Instruments, Dallas, Tex. This type of spatial light modulator is used in the illumination path to change the light pattern as needed for the mapping sequence.

Figure 5:
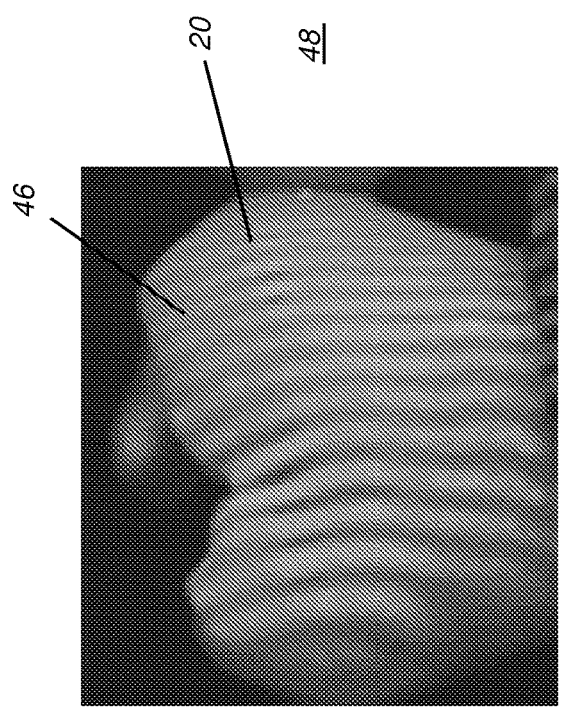
FIG. 5 is a plan view showing projection of a structured light pattern onto a tooth.

The plan view of FIG. 5 shows a typical contour image 48 with projected pattern 46 on a tooth surface 20. As FIG. 5 shows, contour lines can be indistinct on various parts of the surface. To help to compensate for this problem and reduce ambiguities and uncertainties in pattern detection, fringe pattern generator 12 (FIG. 3) typically provides a sequence of patterned images, with the light and dark lines shifted to different positions as described with reference to FIG. 4B and, alternately, having different line thicknesses or distances between lines of light. Various sequences and patterns can be used. It should be noted that a number of variations are possible for providing an ordered set of structured light patterns within the scope of the present disclosure. According to exemplary embodiments, the number of structured patterned images in the ordered set that is projected exceeds 20 images, however, sequences that use more than 20 images or fewer than 20 images could also be used.

Figure 6B:
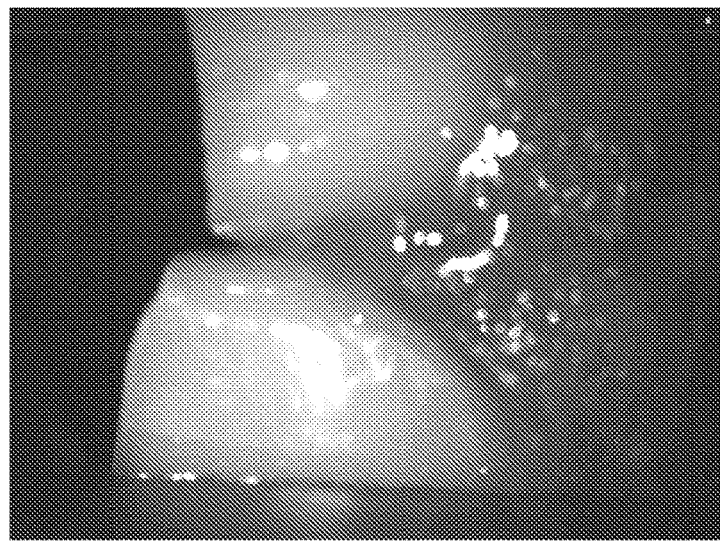
FIGS. 6A, 6B, and 6C show images of teeth obtained on a monochrome image sensor array using light of different spectral bands.
Figure 6A:
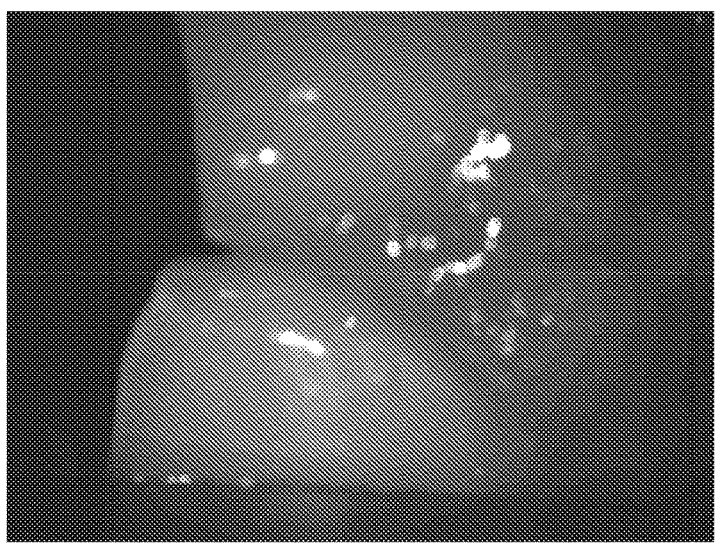
Figure 6C:
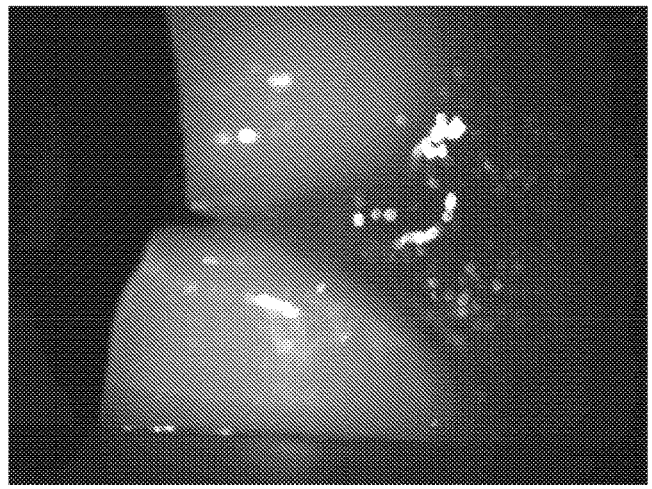

Calibration is provided for the image content, adjusting the obtained image data to generate accurate color for each image pixel. FIGS. 6A, 6B, and 6C show component grayscale or monochrome images 90r, 90g, and 90b of teeth obtained on monochrome sensor array 30 using red, green, and blue light from light sources 32r, 32g, and 32b (FIG. 3) respectively. A grayscale representation of a color image can be formed by combining calibrated image data content for the red, green, and blue illumination. Color calibration data, such as using a linear calibration matrix or other calibration mechanism, can be of particular value where a monochrome sensor is used to obtain color data and helps to compensate for inherent response characteristics of the sensor array for different wavelengths.

There have been a number of 3-D reconstruction apparatus and methods to capture 3-D models of teeth, some of which actually collect the 3-D geometric information from the tooth surface. There have also been a number of apparatus disclosed for capturing photographs of the teeth surface, e.g., color images, which actually reflect the spectrum properties of teeth surfaces for given illumination sources. Method and/or apparatus embodiments of the application described herein can help to improve the user experience and/or provide enhancement of surface details and/or color texture in combining the 3-D geometric information and color image content.

Apparatus and/or method embodiments herein can capture shading images and/or perform texture mapping for 3-D modeling of teeth. Exemplary apparatus embodiments can use only monochrome sensors and one or more illumination sources to compose the color shading images, combined from monochrome shading images. A feature-point matching can register selected/all shading images and employ a texture mapping method to make displayed 3-D teeth model vivid to the observer and/or useful for assisting the diagnosis and treatment process.

Figure 7A:
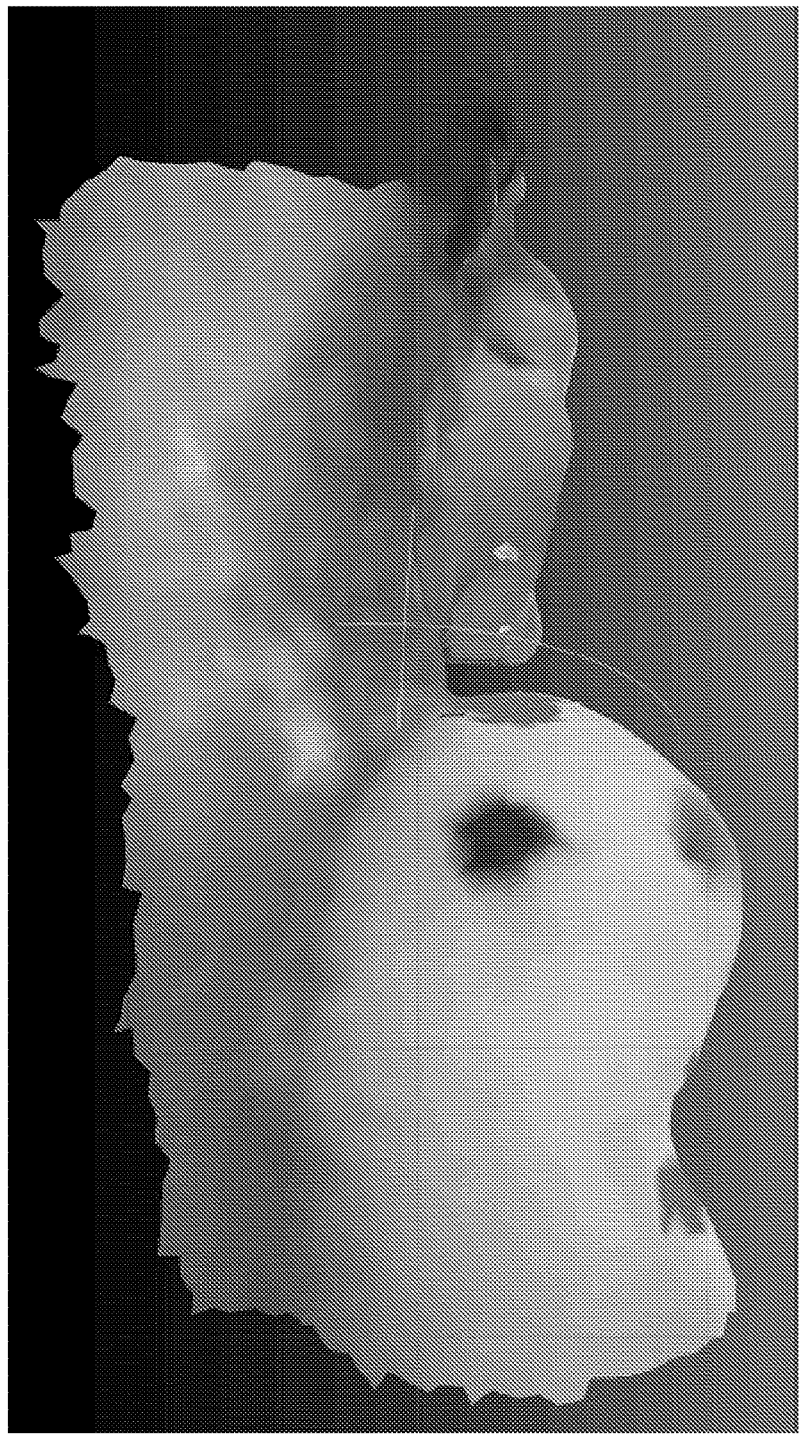
FIG. 7A is a diagram that shows a mesh rendered without texture mapping.
Figure 7B:
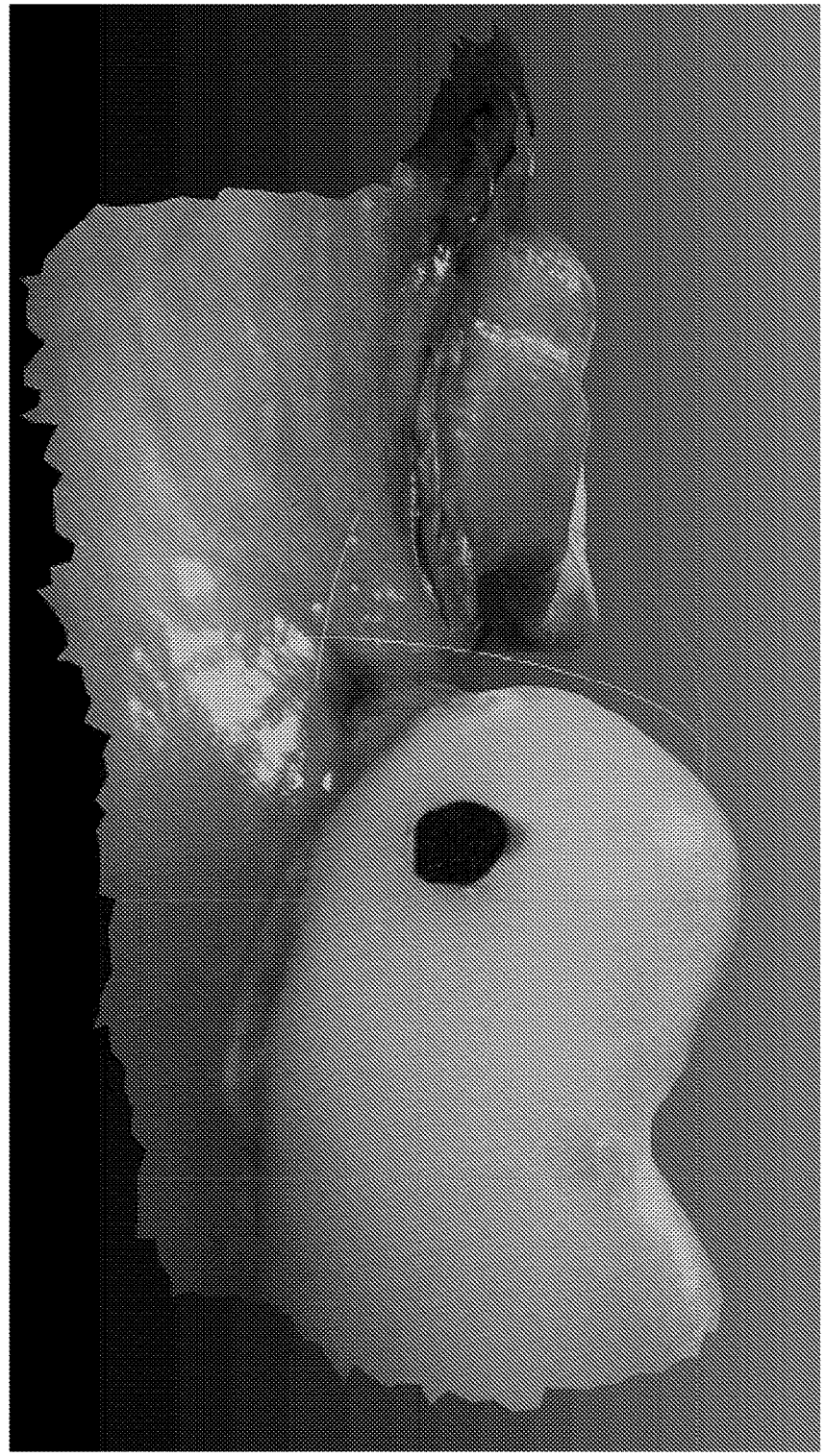
FIG. 7B is a diagram that shows a mesh rendered with texture mapping.

Currently, some of the conventional 3-D dental scanners use a color mapping scheme that assigns a color value to each vertex in the 3-D tooth model. This type of vertex/color assignment can be a poor compromise, however, and often provides an approximation of color that is disappointing, making it difficult to observe more complex surface detail information and color texture. An example of the results of existing 3-D dental scanners is shown in FIG. 7A. In contrast to FIG. 7A, an example of texture mapping results on teeth according to exemplary method and/or apparatus embodiments of the application is shown in FIG. 7B. As suggested by FIGS. 7A and 7B, and particularly noticeable when presented in color, exemplary texture mapping methods and/or apparatus of the application provide a more accurate and/or more realistic representation of the surface appearance for tooth structures than do vertex mapping techniques.

Overview of Processing Sequences

According to exemplary apparatus and/or method embodiments, a number of views of teeth and surrounding structures can be captured. These can include a group of structured-light patterns for each view, projected onto tooth surfaces in sequence, with a corresponding set of fringe images acquired. Based on correspondence between projected patterns and captured fringe images, triangulation is performed to generate a 3-D point cloud of the teeth, using techniques familiar to those skilled in the art of contour imaging. For each view, LED or other light sources having specified wavelength or color spectrum bands are used to illuminate the teeth through an optical path in an ordered sequence. In addition, a set of monochromatic component shading images are captured by a monochrome sensor in sequence. 2-D feature points are extracted from the monochrome images. Transformations between the shading images are calculated, by which the monochromatic component shading images are registered to each other, such as using the extracted feature points. In one embodiment, using a pre-specified color linear calibration matrix, the color value for each pixel is recovered from the combined, registered pixel values taken from the shading images. Thus, for each view, a color shading image is also generated.

After mesh-generation, matching, merging, and 3-D mesh noise suppression, 3-D point clouds generated in all views can be combined to generate the final 3-D mesh surfaces for the subject teeth. This final 3-D mesh defines a number of faces, each face defined by its nearest 3-D vertices, so that each face is planar and has a triangular construction, although more generally, each face is planar and has a polygonal shape formed from three or more sides. A point cloud of a surface can be used to define a triangular mesh and, optionally, a mesh having other polygonal shapes. The triangular mesh is the most geometrically primitive mesh and generally allows the most straightforward computation of polygonal shapes. The multiple combined faces extend across the surface of teeth and related structures and thus, plane section by plane section, define the surface contour. As part of this processing, the visibility of each face in the mesh is determined and matched to the particular view that provides best observation on the faces in all views. The full set of views matched by all faces in the mesh serves as the key view frame. The term "key" relates to the use of a particular image view as a type of "color key", a resource used for color mapping, as the term is used by those skilled in the color imaging arts. A key view is a stored image taken at a particular aspect and used for texture mapping, as described in more detail subsequently.

Using mesh post-processing techniques, faces from the 3-D mesh are separated into groups called "texture fragments", wherein the faces in a particular texture fragment all geometrically connect to other faces in the same fragment and are assigned to the same key view. According to an exemplary embodiment of the present disclosure, post-processing methods can be used to enhance the smoothness of boundaries between each texture fragment. This processing can be performed fragment by fragment, one at a time. In processing each fragment, the vertices that define the fragment are projected onto its view (e.g., its key view) using a standard projection routine, employing techniques well known for mapping 3-D points to a 2-D plane. This projection can also use the camera's intrinsic parameters extracted as part of camera calibration.

The projected image coordinates of vertices are used as their texture coordinates. In one exemplary embodiment, all boundaries between texture fragments are also projected onto views in the key view. Using corresponding color data from each key view, a color blending method can be performed on the projected boundary in order to reduce color discrepancies and/or to correct for any color discrepancy between views due to the mapping.

From this mapping and blending process, regions in color shading images corresponding to the projected texture fragments for each of the views can be extracted and packed into a single texture image, termed a "global texture map". In one exemplary embodiment, a packing strategy can be used to make the packed texture image more compact and/or more efficient. The texture coordinates of all vertices can also be adjusted so that they align to the origin of the global texture map.

For certain exemplary embodiments, all vertices with 3-D coordinates and 2-D texture coordinates and the global texture map can be output to a 3-D rendering engine for display, using techniques familiar to those skilled in volume image representation. Results can also be stored in memory or transmitted between processors.

Sequences used in certain exemplary apparatus and/or method embodiments are described in more detail in exemplary steps that follow.

Part 1. Form the Color Shading Images

This first part of this procedure acquires the component monochrome images (e.g., using camera 40 (FIG. 1)) and can combine them to generate the composite color shading images for a particular view of the teeth.

Figure 8A:
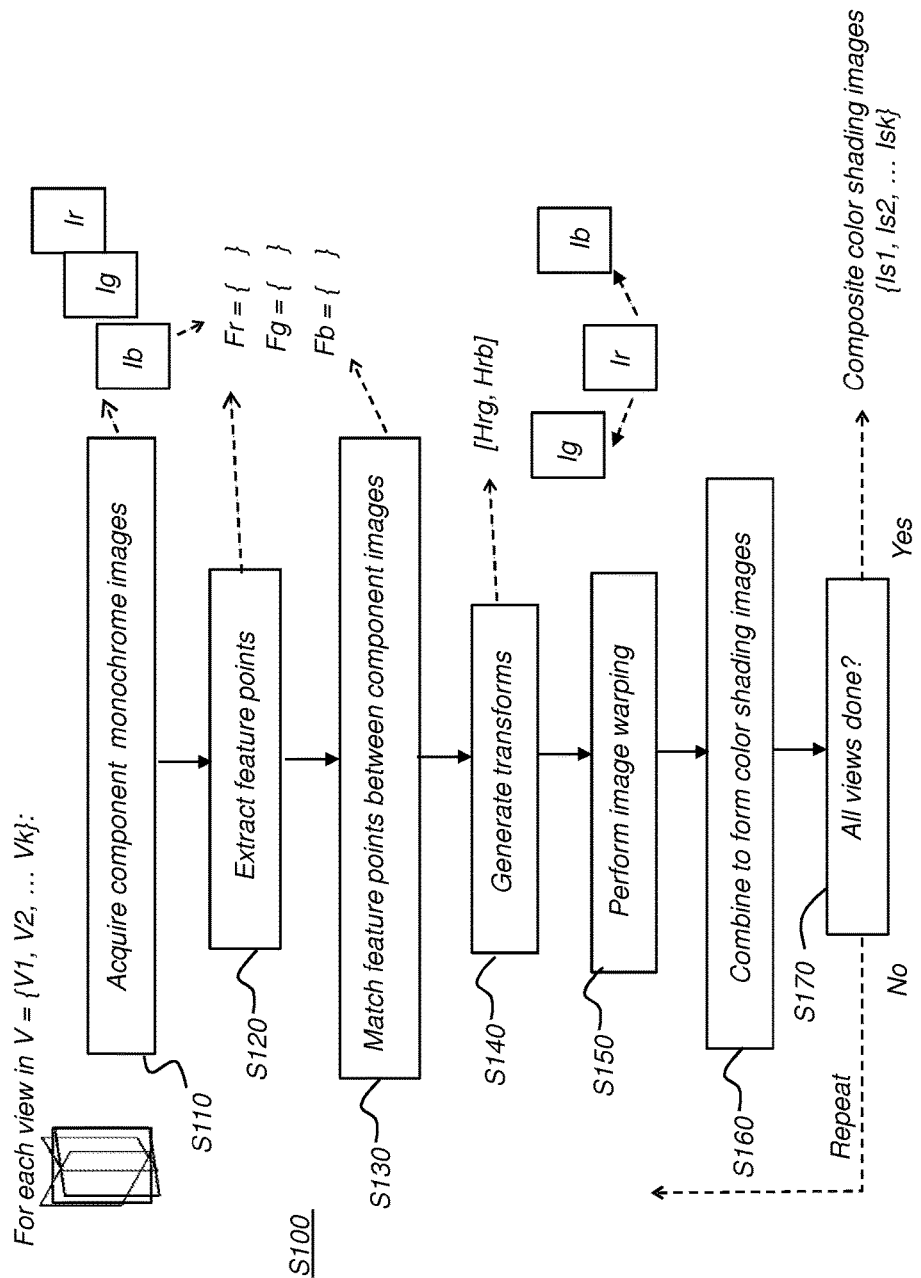
FIG. 8A is a logic flow diagram that shows processing for forming composite color shading images.

FIG. 8A is a logic flow diagram that shows exemplary processing for forming composite color shading images {Is1, Is2, ... Isk}. This processing can be executed for each of the K views of the tooth obtained from reflectance imaging that obtains both contour images and color image content. The process of composite color shading image set generation step S100 can begin with a set of views V:

V={V1, V2, ..., Vk}, each view at a different view pose, wherein pose for a particular view relates to its viewing aspect; the phrase "view pose" or "view aspect" relates to orientation alignment and positional characteristics such as the relative amounts of roll, yaw, and pitch of the subject relative to a coordinate system having its origin at a focal point of the camera, and includes characteristics such as view distance and camera angle. One exemplary method then executes a sequence that generates a set of K corresponding component color shading images:

{Is1, Is2, ... Isk}.

Sub-steps of Part 1, executed for each view, can be as follows:
1) In an image acquisition step S110, acquire each of the component monochrome images, Ir, Ig, Ib, capturing them using different (e.g., Red, Green, and Blue) color illumination, respectively.
2) Extract feature points from the captured component monochrome images in a feature points extraction step S120. Feature points extraction step S120 may use, for example, Harris & Stephens corner detection or other feature detection technique known to those skilled in the image feature detection arts. Feature points can be extracted from each of the component monochrome images Ir, Ig, Ib, to generate three corresponding sets of feature points:

Fr={Pr1, Pr2, ... PrN};

Fg={Pg1, Pg2, ..., PgM}; and

Fb={Pb1, Pb2, ..., PbL}.

3) In a matching step S130, selected searching and matching techniques can be used to match the three sets of feature points. One method, for example, first matches set of feature points Fr with set Fg, and then matches set Fr with Fb, employing Normalized Cross-Correlation of the local region in component monochrome images Ir, Ig, Ib around each extracted feature point. According to one embodiment, RANSAC (a well-known random sample consensus algorithm) can be adopted to reduce the influence of outliers in the matching introduced in step S130.

4) In a transform generation step S140, using homograph estimation or other suitable tools, calculate at least two two robust linear transforms Hrg for Ir-Ig and Hrb for Ir-Ib mapping.
5) Using the calculated transforms Hrg and Hrb from step S140, perform image warping on monochrome images Ig and Ib in an image warping step S150. Image warping step S150 can align the component images, such as aligning both Ig and Ib to Ir.
6) Combine Ir and aligned Ig and aligned Ib in a combining step S160 to form a composite color shading image.

A decision step S170 can determine whether or not each view has been processed using the composite color shading image set generation step S100 procedures. Processing repeats for each view.

Combining a set of the at least three monochromatic shading images can generate a composite 2-D color shading image, wherein each 2-D color shading image has color texture information or image structure information including color and additional appearance attributes, and an associated view pose.

Part 2. Mesh Generation and Processing

Figure 8B:
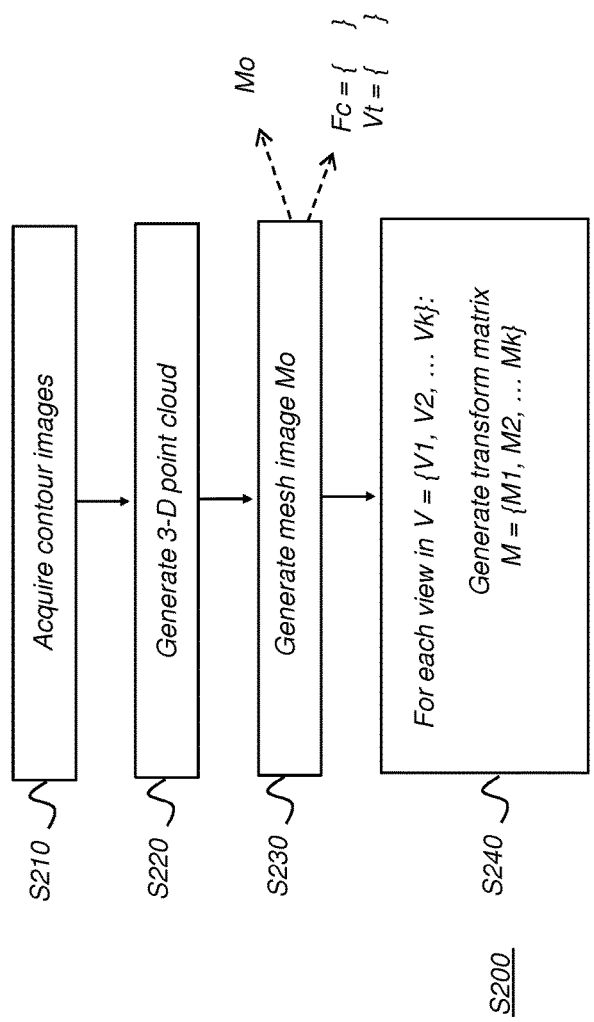
FIG. 8B is a logic flow diagram that shows processing for generating and using mesh information.

Mesh processing procedures can be used to generate the mesh and to match, merge, and provide noise suppression in order to acquire the final output mesh, Mo. FIG. 8B is a logic flow diagram that shows exemplary processing for generating and using mesh information in a mesh generation step S200.

Figure 8C:
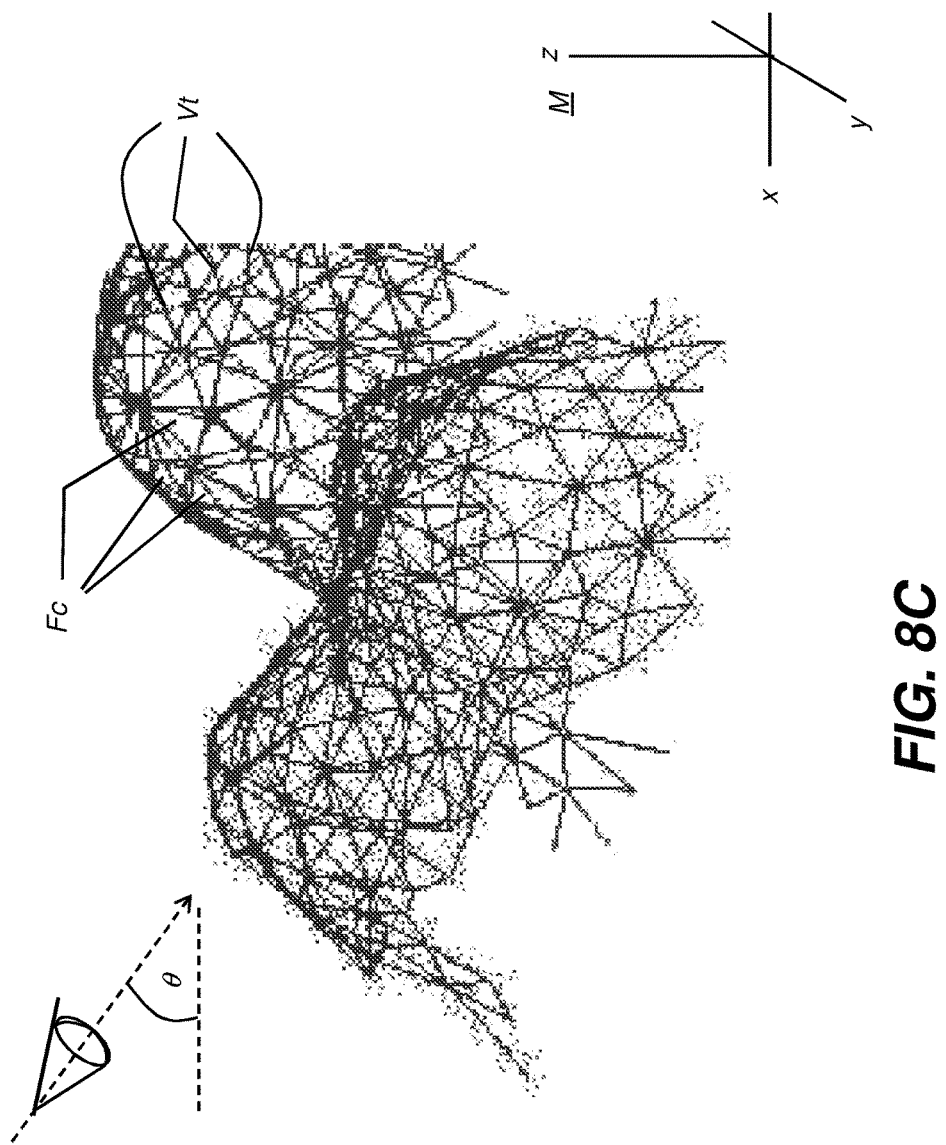
FIG. 8C is a perspective view showing a portion of a mesh with planar faces as generated according to an exemplary embodiment of the application.

In an image acquisition step S210, structured light images for contour imaging are obtained. A point cloud generation step S220 then generates a 3-D point cloud from structured light images. Mesh information is combined in order to generate final output mesh Mo in a mesh generation step S230. FIG. 8C shows a mesh M with individual planar faces Fc. Each face Fc is triangular in the example shown. FIG. 8C also shows the pose relative to mesh M.

Each triangular (planar) face Fc in the mesh is defined using three vertices Vt. Mesh Mo has a total of J planar faces Fc and I vertices Vt:

Fc={Fc1, Fc2, ... FcJ}

Vt={Vt1, Vt2, ... VtI}.

For each view in V={V1,V2, ..., Vk}, in a transform matrix generation step S240, this processing also generates its transform matrix M relative to Mo:

M={M1, M2, ..., Mk}

Using the corresponding transform matrix from this set, each of faces Fc and vertices Vt can be transformed into the coordinate system of each view V.

Figure 8D:
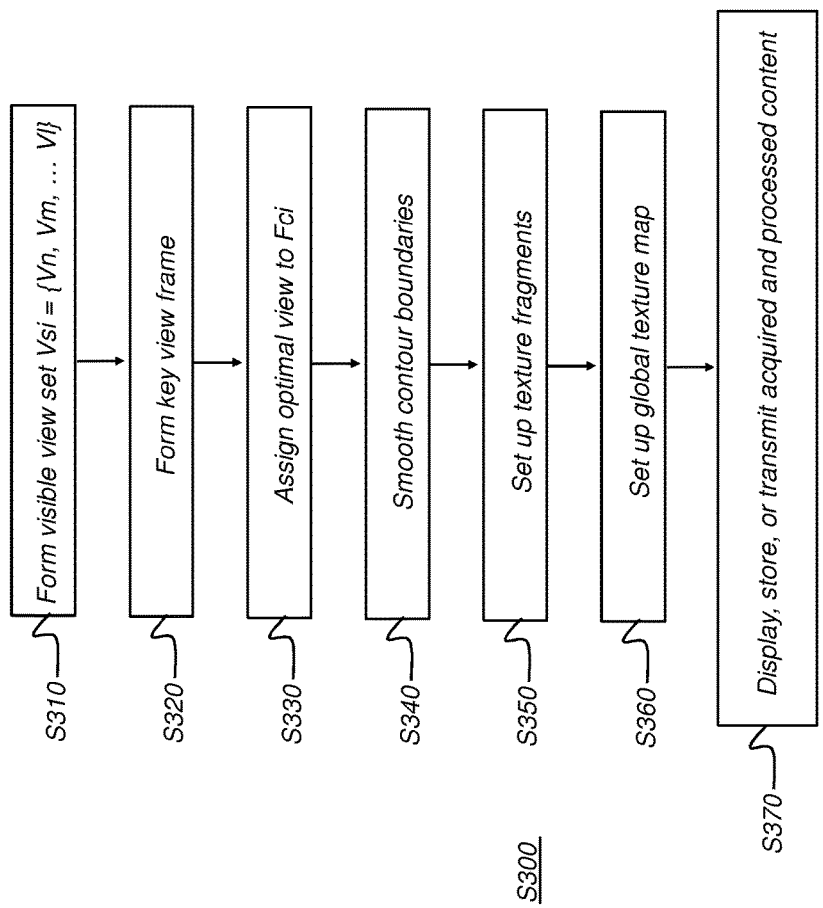
FIG. 8D is a logic flow diagram that shows processing for generating a global texture map.

FIG. 8D is a logic flow diagram that shows subsequent processing in an exemplary global texture map generation step S300, with exemplary procedures for forming a key view frame (Part 3), view assignment of faces (Part 4), generating a global texture map, contour smoothing (Part 5), and texture fragments setup (Part 6).

Part 3. Exemplary key view frame setup

At this point in processing, the key view frame can be identified, using the following exemplary sequence, shown as form visible view step S310 and key frame setup step S320 in the logic flow diagram of FIG. 8D:
1) For each face Fci in the final output mesh Mo, determine in which views V the face Fci is visible. In form visible view step S310, form the visible view set VS_i of Fci:

VS_i={Vn, Vm, ..., Vl}.

This determination can use visibility criteria such as the following:
- a) The normal of face Fci must be closer to the viewing direction of VS_i than a pre-defined threshold, Th_n;
- b) Face Fci must be in the field of view (FOV) of visible view set VS_i;
- c) Fci must be closer to the focus plane of visible view set VS_i than a pre-defined threshold, Th_f;

However, alternate visibility criteria can be applied.

2) Using visible view set VS_i for Fc, identify and remove views that overlap excessively. For example, if two views contain an excessive number of identical faces, one of the views is redundant and can be removed. In exemplary key frame setup step S320, the remaining views V can be used to form the key view frame as set:

$$Vk=\{Vk1, Vk2, \ldots Vkp\};$$

this set can contain views V Vkn that slightly overlap each other.

3) If some views V exclusively contain certain faces, these views can preferably be added to the key view frame Vk.

4) Prune the Vk set to preferably ensure no redundant view V exists in Vk. For example, check each view Vkn in Vk. If, without a particular Vkn, all faces can still be visible for remaining views in Vk, then remove that Vkn.

Part 4. Exemplary View Assignment of Faces

Figure 9:
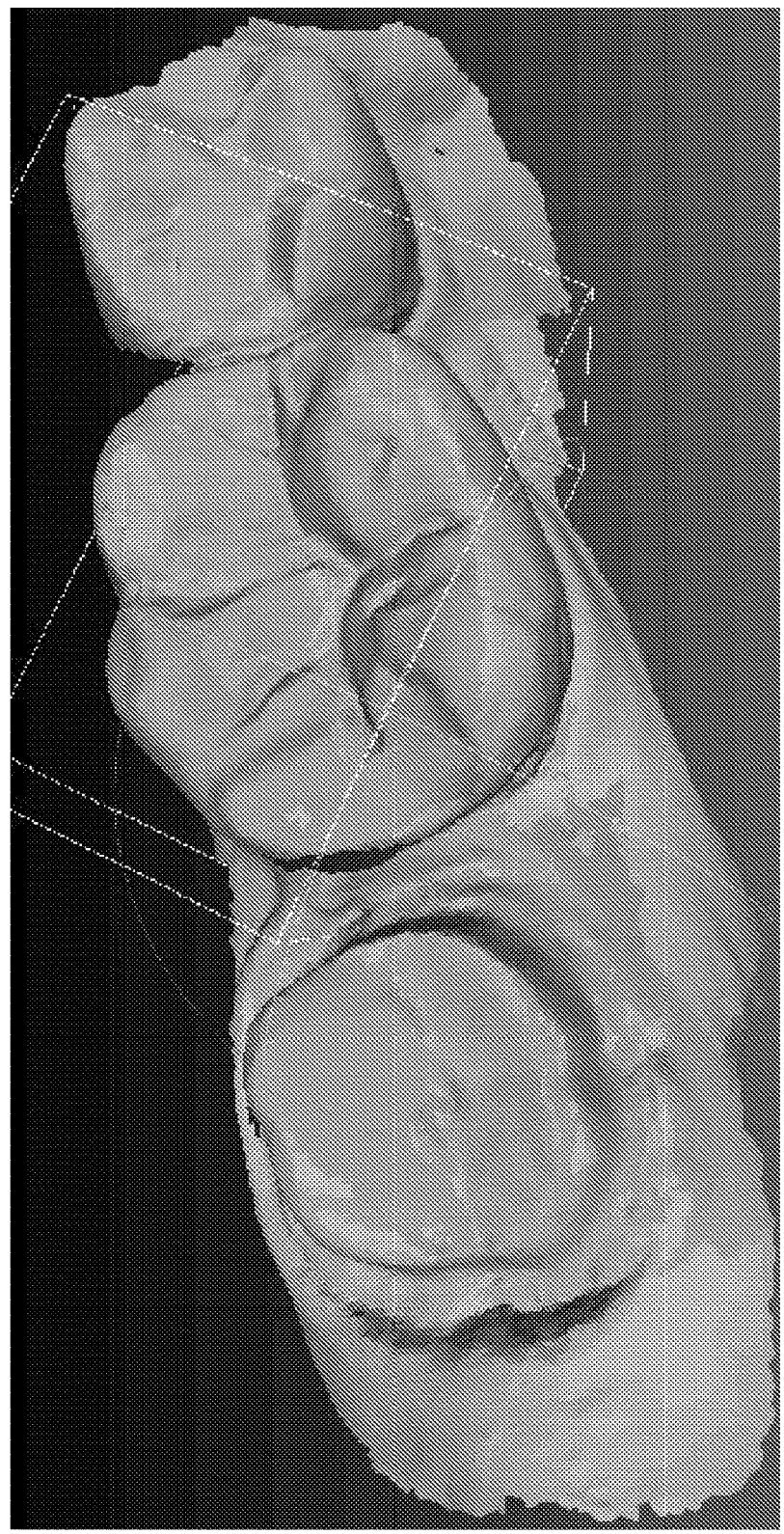
FIG. 9 is a diagram that shows a view of assignment of faces.

Part 4 describes portions of exemplary view assignment step S330 of the FIG. 8D procedure. FIG. 9 shows an example of desired/selected view assignment of faces obtained from this Part.

1) For each face Fci in final output mesh Mo, determine in which views V the face Fci is visible using the criteria given below. These views form the visible view set VS of Fci:

$$VS\_i=\{Vn, Vm, \ldots, Vl\}.$$

Exemplary criteria and parameters for determining visibility can include the following:
- d) Normal score: The normal of Fci must be closer to the viewing direction of VS_i than a pre-defined threshold, Th_n1;
- e) FOV: Fci must be in the FOV of VS_i;
- f) Focus score: Fci must be closer to the focus plane of VS_i than a pre-defined threshold, Th_f2.

It can be appreciated that alternate visibility criteria can be used.

2) Combine the normal score and focus score for all VS_i as the assigning score;

3) Select one view with the best assigning score (e.g., the optimal view) as the assigned view of Fci.

For example, the results of view assignment appear as shown in the example of FIG. 9. Here, meshes in the same color (or shade, grayscale, texture, marking or pattern, etc.) represent the faces assigned to same view.

Part 5. Exemplary Contour Refine for the View Assignment of Faces in Final Output Mesh Mo This next sequence of steps performs contour and boundary smoothing in an exemplary contour smoothing step S340 (FIG. 8D) for the view assignment of faces.

Figures 10A, 10B:
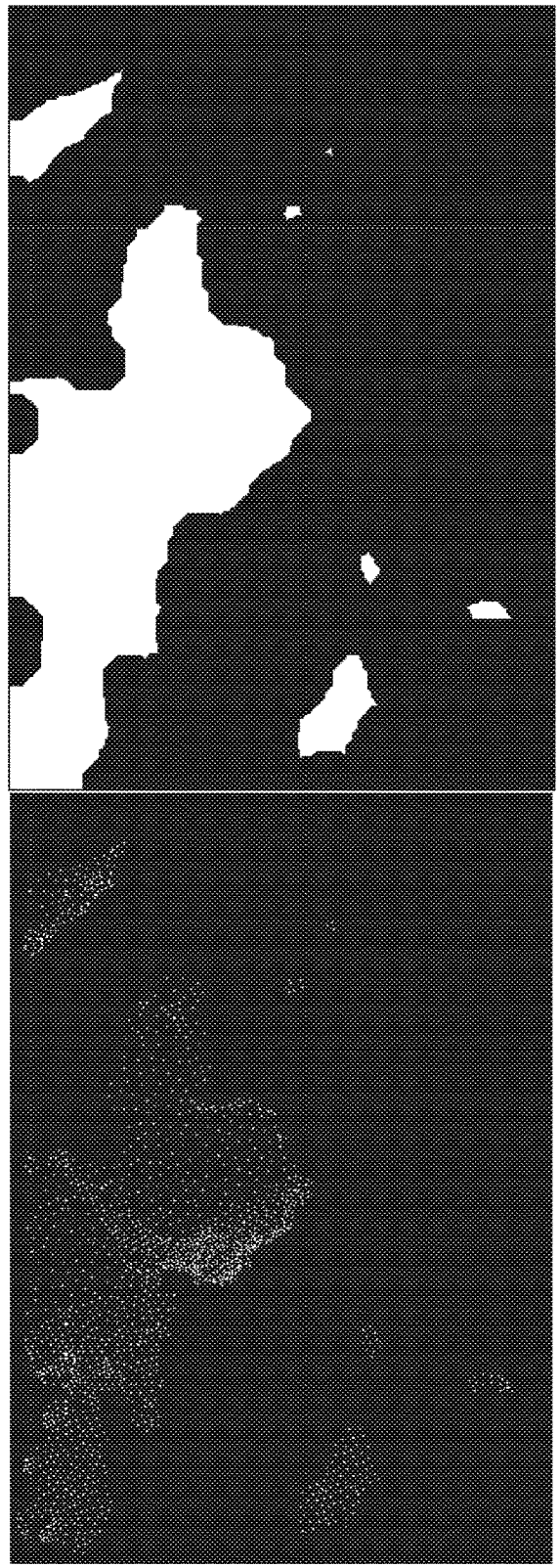
FIG. 10A is a diagram that shows vertices projection.
FIG. 10B is a diagram that shows vertices projection after 2-D processing.

1) For each view Vj in the key view frame, project all vertices of faces assigned to Vk onto imaging plane Isj of Vj to acquire a binary image, Isbj, wherein the 2-D projected vertices are marked as TRUE (bright) and background pixels are marked as FALSE (black), as shown in FIG. 10A. Then mathematic morphological operations can be executed on image Isbj to acquire the binary image, Imsbj as shown in FIG. 10B. Then, for each vertex, visibility for Vj is checked, as was done in Part 3. All vertices visible to Vj are projected onto image Imsbj. For any vertex V to that is visible to Vj, wherein its projected 2-D point in image Imsbj is TRUE, the vertex V to is assigned to the view Vj.

In certain embodiments, projection of 3-D vertices to their corresponding 2-D coordinates is based on intrinsic parameters estimated in advance and/or on extrinsic parameters established in Part 2.

2) For each face Fci, processing can check the view assignment of its three neighboring or adjacent faces, that is, each face that shares an edge in common with Fci. If the three neighboring faces are all assigned to the same view as Fci, no action is taken. Otherwise, the view assignment Vk that is in the majority of the three neighbors is identified and face Fci assigned to view Vk in the key view frame.

Part 6. Exemplary Texture Fragments Setup

The next part of this procedure sets up texture fragments that group a set of faces to the same key view as part of an exemplary texture fragments setup step S350 in FIG. 8D.

1) For each view Vj, project all vertices assigned to Vj onto the imaging plane associated with Vj to acquire a binary image, Isbj, as shown in FIG. 10A.

Figure 11:
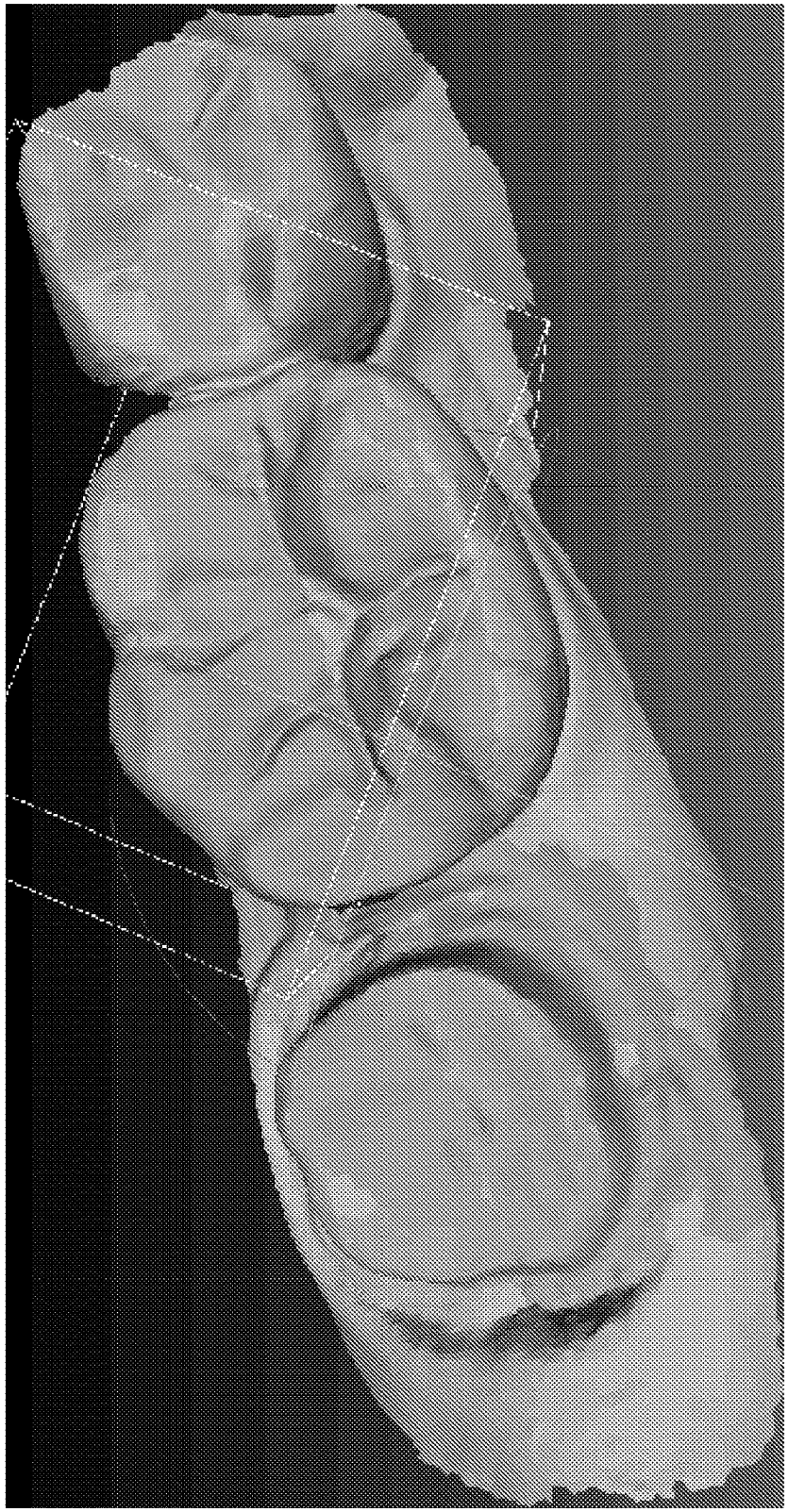
FIG. 11 is a diagram that shows the meshes represented by texture fragments.

2) Acquire connected components, as shown in FIG. 10B, using processing such as binary image dilation and binary image erosion on Isbj. Parameters for dilation and erosion, including the size of structure elements, thresholds, and other parameters that affect dilation and erosion performance, can differ from those used in Part 4. Then, use image connected component labeling to extract all components in image Isbj. For example, the faces and vertices projected into the same component are arranged as the same texture fragment. In this way, texture fragments can be established, and the full mesh Mo can correspond to a set of texture fragments, Fg={Fg1, Fg2, . . . , Fgw}. FIG. 11 shows mesh elements represented by texture fragments, with each color or grayscale shade indicating a particular texture fragment.

In one embodiment, each texture fragment contains the faces Fci and vertices Vt assigned to the same view in the key view frame and sharing the same region in the color shading image. The texture coordinates of each vertex Vt that project onto the view and the bounding box of the projection are also contained in the texture fragment.

Part 7. Exemplary Vertex Texture Coordinates Generation

For each texture fragment Fgi in set Fg, its faces and vertices are projected onto its assigned view, recording the projected image coordinates, (e.g., this is performed similar to Part 5).

Part 8. Exemplary Color Blending for Texture Fragments

In one embodiment, processing extracts the boundary faces of all texture fragments using the following exemplary strategy:

1) For each face Fci in all texture fragments check the view-assignment of its three neighboring faces that share a common edge with the face Fci.

If the neighboring faces are all assigned to the same view as Fci, do nothing. Otherwise, label or mark the face Fci as a boundary face.

2) Identify edges in the boundary faces that link two faces assigned to different texture fragments. This defines a group of edges:

Eg={Eg1, Eg2, . . . , EgN}.

Each edge contains the two ending vertices.
3) Identify the vertex coordinates UV in two views at two sides of the edges:

Egk={Egidk, Vk1, UV1k1, UV2k1, Vk2, UV1k2, UV2k2}

Figure 12A:
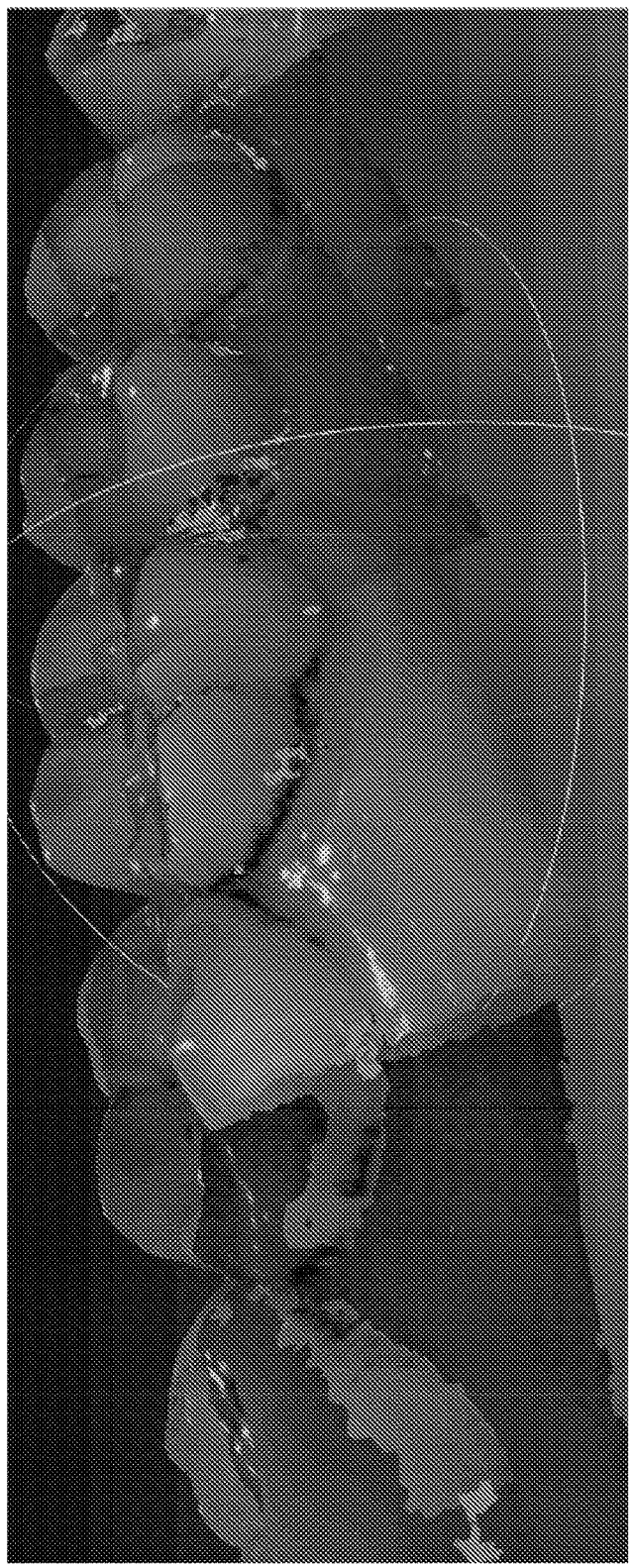
FIG. 12A is a diagram that shows textured mesh without color blending.
Figure 12B:
FIG. 12B is a diagram that shows the final textured mesh after color blending.

Wherein:
  Egidk is the index of an edge in the set Eg;
  Vk1 and Vk2 are indices of two views linked by Egk in the key view frame;
  UV1$k$1 and UV2$k$1 are the texture coordinates of two ending vertices of Egk.
4) For each edge and each fragment (as the current fragment), execute exemplary color blending as follows:
  4a) Fetch the color value C1$k$1 and C2$k$1 at position of coordinates UV1$k$1 and UV2$k$1 in the color shading image Isk1 and color value C1K2 and C2$k$2 at UV1$k$2 and UV2$k$2 in color shading image Isk2. Assume that the current fragment is assigned to Isk1.
  4b) Set the target color values at UV1$k$1 and UV2$k$1 with the weighted average of C1$k$1 and C1$k$2; and C2$k$1 and C2$k$2, respectively. At the same time, also calculate the difference between the current color value and target color value.
  4c) For all pixels on the 2d line linking texture coordinates UV1$k$1 and UV2$k$1, calculate a color difference using bi-linear interpolation and the color difference at coordinates UV1$k$1 and UV2$k$1 calculated in 4b). The pixels on lines of all projected edges of the current fragment define an enclosed contour, termed an edge contour, of current fragments on images. The pixel values are used as the boundary condition for the following sub-step.
  4d) Based on the above boundary condition, an interpolation can be performed to calculate the pixel value for all pixels bounded by the edge contour. The interpolated pixel value is the smoothed color difference for each pixel bounded within the edge contour.
  4e) For each pixel inside the current fragment, apply the interpolated color difference to the original color value of the pixel in color shading image Isk1 to generate the color blending version Isk_adj_1 as the final shading image for the current fragment. Results from before and after color blending appear as shown in the examples of FIG. 12A and FIG. 12B.

Part 9. Exemplary Extraction and Packing of Texture Fragment Regions in Blended Color Shading Images of Key Views.

The procedure given here can complete an exemplary global texture map setup step S360 in the FIG. 8D process.

For certain embodiments, a dual-lists strategy can be used to pack all texture fragments:
1) Initialize a blank image as the global texture map, Itm, with the width of Wtm and height of Htm;
2) Sort all texture fragments according to the relative size of their bounding box, as recorded in Part 6.
3) For each texture fragment, perform the following:
  If, at the current position including column and row coordinates in Itm, space including width and height is available for the bounding box of the current texture fragment, copy, into the current position in global texture map Itm, the region in the texture fragment's blended color shading image specified by the bounding box. Record the right column and row coordinate of the copied region in the next list. Otherwise, if space is not available, find a new row position at the current scanning location using the current list to prevent overlapping.
  If at the current scanning position, there is not enough width for the bounding box of the current fragment, go to the next scanning position in global texture map Itm. Switch the next list and current list. Determine the current available position. Adjust the texture coordinates of all vertices for alignment to the global texture map.

Figure 13:
FIG. 13 is a diagram that shows the binary illustration of the global texture map.

Exemplary results of Part 9 provide a mapping as shown in FIG. 13. This example shows a global texture map Itm binary image that illustrates the patches of all texture fragments.

Using a Global Texture Map

Once the global texture map is generated, the global texture map can be used to help speed image generation and provide texture content for a given view of a tooth and related structures. A global texture map is specified according to the desired view for display of the tooth image in step S370 (FIG. 8D). Then, to populate each visible face in the view with texture content, the global texture map provides a quick reference to the appropriate key view for the appearance of that face.

The global texture map can be considered a scaled or reduced size representation that shows portions of the 2-D texture shading images as correlated to the texture fragments. The texture map is used for rendering the color texture 3-D surface contour image of the teeth.

In processing, the global texture map can effectively provide a type of two-dimensional look—up table for visible faces in a given view. Providing a quick reference to image content in this way allows re-creation of a particular view to proceed quickly, without the need for considerable re-computation when changing the view angle or perspective, as with other related art texture-mapping schemes. Thus, in certain exemplary embodiments, rotation or movement of the image can appear to be performed in real time, without requiring extensive computing resources.

Consistent with selected exemplary embodiments of the application, a computer executes a program with stored instructions that perform on image data accessed from an electronic memory. As can be appreciated by those skilled in the image processing arts, a computer program of an exemplary embodiment of the application can be utilized by a suitable, general-purpose computer system, such as a personal computer or workstation, as well as by a microprocessor or other dedicated processor or programmable logic device. However, many other types of computer systems can be used to execute the computer program of the application, including networked processors. The computer program for performing the method of the application may be stored in a computer readable storage medium. This medium may comprise, for example; magnetic storage media such as a magnetic disk (such as a hard drive) or magnetic tape or other portable type of magnetic disk; optical storage media such as an optical disc, optical tape, or machine readable bar code; solid state electronic storage devices such as random access memory (RAM), or read only memory (ROM); or any other physical device or medium employed to store a computer program. The computer program for performing exemplary method embodiments of the application may also be stored on computer readable storage medium that is connected to the image processor by way of the internet or other communication medium. Those skilled in the art will readily recognize that the equivalent of such a computer program product may also be constructed in hardware.

It will be understood that the computer program product of the application may make use of various image manipulation algorithms and processes that are well known. It will be further understood that exemplary computer program product embodiments of the application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with computer program products of the application, are not specifically shown or described herein and may be selected from such algorithms, systems, hardware, components and elements known in the art.

In the context of the present disclosure, the act of "recording" images means storing image data in some type of memory circuit in order to use this image data for subsequent processing. The recorded image data itself may be stored more permanently or discarded once it is no longer needed for further processing.

It should be noted that the term "memory", equivalent to "computer-accessible memory" in the context of the present disclosure, can refer to any type of temporary or more enduring data storage workspace used for storing and operating upon image data and accessible to a computer system. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types. Computer-accessible memory of various types is provided on different components throughout the system for storing, processing, transferring, and displaying data, and for other functions.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim.

In the following claims, the terms "first," "second," and "third," and the like, are used merely as labels, and are not intended to impose numerical requirements on their objects.

Method and/or apparatus embodiments according to the application can provide full color texture mapping in an intra-oral 3-D scanner with a monochrome sensor.

Although exemplary embodiments were described using triangular faces of 3-D mesh, other polygonal shapes can be used for the planar faces. Although exemplary embodiments were described for the 3-D IO scanner system based on triangulation methods to form the 3-D mesh, this application in not intended to be so limited, for example, the 3-D mesh can be generated from any conventional 3-D scanning methods (e.g., confocal imaging methods or multi-view or stereoscopic imaging methods). Exemplary embodiments according to the application can include various features described herein (individually or in combination).

In one embodiment, a method for forming a color texture mapping to a 3-D contour image of one or more teeth in a intra-oral camera with a monochrome sensor array, can include obtaining a 3-D mesh representing a 3-D surface contour image of the one or more teeth according to recorded image data; generating a plurality of sets of at least three monochromatic shading images by projecting light of at least three different spectral bands onto the one or more teeth and recording at least three corresponding color component image data on the monochrome sensor array; combining selected sets of the at least three monochromatic shading images to generate a plurality of corresponding 2-D color texture shading images, where each of the plurality of color texture shading images has a view to the one or more teeth; assigning each 3-D mesh polygonal surface in the 3-D mesh representing the 3-D surface contour image of the one or more teeth to one of a subset of the 2-D color texture shading images; grouping 3-D mesh polygonal surfaces assigned to the same 2-D color texture shading image into a 3-D mesh fragment surface; determining representative coordinates for each of the 3-D mesh fragment surfaces in the assigned 2-D color texture shading image; and rendering the 3-D mesh polygonal surfaces with the color texture values from the 3-D mesh fragment surfaces according to the determined coordinates in the assigned 2-D color texture shading image to generate a color texture 3-D surface contour image of the one or more teeth. In one embodiment, assigning each 3-D mesh polygonal surface forming the 3-D surface contour image of the one or more teeth to said one 2-D color texture shading images can include identifying 3-D mesh polygonal (e.g. triangular) surfaces forming the 3-D surface contour image of the one or more teeth; matching a first subset of 2-D color texture shading images by orientation alignment to a single one of the 3-D mesh polygonal surfaces; and determining 3-D mesh fragment surfaces by grouping remaining ones of the 3-D mesh polygonal surfaces to a single one of the matched 3-D mesh polygonal surfaces. In one embodiment, determining representative coordinates for each of the 3-D mesh fragment surfaces can include projection of the 3-D mesh fragment surface coordinates into the assigned 2-D color texture shading image.

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims, and all changes that come within the meaning and range of equivalents thereof are intended to be embraced therein.

The invention claimed is:

1. A method for color texture mapping to a 3-D contour image of one or more teeth captured by an intra-oral camera with a monochrome sensor array, comprising:
   obtaining a 3-D mesh including a plurality of polygonal surfaces representing a 3-D surface contour image of the one or more teeth according to image data recorded from a plurality of views of the one or more teeth, wherein for each of the plurality of views, recording image data comprises generating a plurality of sets of at least three monochromatic shading images by projecting light of at least three different spectral bands onto the one or more teeth and recording the corresponding image data on the monochrome sensor array;
   combining each set of the plurality of sets of at least three monochromatic shading images to generate a plurality of 2-D color shading images, where each of the plurality of 2-D color shading images corresponds to one view of the plurality of views;
   assigning selected polygonal surfaces of the plurality of polygonal surfaces in the 3-D mesh representing the 3-D surface contour image of the one or more teeth to one view of a subset of the plurality of views;
   grouping 3-D mesh polygonal surfaces assigned to the same view into a texture fragment of a plurality of texture fragments;
   determining image coordinates for vertices of the 3-D mesh polygonal surfaces in each texture fragment from projection of the vertices onto the view associated with the texture fragment; and
   rendering the 3-D mesh with texture values in the 2-D color shading images corresponding to each texture fragment according to the determined image coordinates to generate a color texture 3-D surface contour image of the one or more teeth.

2. The method of claim 1, where the assigning selected polygonal surfaces of the plurality of polygonal surfaces forming the 3-D surface contour image of the one or more teeth to said one view of the plurality of views comprises:
   identifying the plurality of polygonal surfaces forming the 3-D surface contour image of the one or more teeth; and
   matching each polygonal surface of the plurality of polygonal surfaces to a view with a closest orientation alignment.

3. The method of claim 1, further comprising storing, transmitting, or displaying the generated color texture 3-D surface contour image of the one or more teeth.

4. The method of claim 1, further comprising
   generating a global texture map for all regions in the 2-D color shading images corresponding to each texture fragment; and
   storing, transmitting, or displaying any of:
   (i) the 3-D mesh representing the 3-D surface contour image of the one or more teeth,
   (ii) the image coordinates associated with the vertices of the polygonal surfaces in said each texture fragment, and
   (iii) the global texture map.

5. The method of claim 4, where the global texture map is a reduced-size representation of portions of the 2-D texture shading images correlated to the plurality of texture fragments, and is used for rendering of the color texture 3-D surface contour image of the one or more teeth.

6. The method of claim 1, further comprising smoothing boundaries between adjacent texture fragment surfaces according to texture values.

7. The method of claim 1, where the combining each set of the plurality of sets of at least three monochromatic shading images comprises:
   registering individual ones of the each set of the plurality of sets of at least three monochromatic shading images to other individual ones of the each set of the plurality of sets of at least three monochromatic shading images; and
   combining data from the registered set of the plurality of sets of at least three monochromatic shading images to generate one color shading image having a single view of the one or more teeth.

8. The method of claim 7, where said registering the individual ones of the each set of the plurality of sets of at least three monochromatic shading images comprises 2-D feature extraction and transformations between the at least three monochromatic shading images.

9. The method of claim 1, where the obtaining the 3-D mesh representing the 3-D surface contour image of the one or more teeth comprises: generating the 3-D mesh according to recorded image data from structured pattern projection onto the one or more teeth.

10. The method of claim 9, where the generating surface contour image comprises, for each of a plurality of structured patterns, projecting the structured pattern onto the one or more teeth and recording image data from the structured pattern onto a monochrome sensor array, where said projecting the structured pattern is performed when the intra-oral camera is moving or still, wherein the plurality of structured patterns include shifted versions of a pattern having multiple lines of light, where projecting the structured pattern comprises energizing a digital micromirror array or energizing a liquid crystal device.

11. The method of claim 1, where the generating a plurality of sets of at least three monochromatic shading images comprises:
   projecting light of a first spectral band onto the one or more teeth and recording a first color component image data on the monochrome sensor array while the monochrome sensor array in the intra-oral camera is moving or still;
   projecting light of a second spectral band onto the one or more teeth and recording a second color component image data on the monochrome sensor array while the monochrome sensor array in the intra-oral camera is moving or still; and
   projecting light of a third spectral band onto the one or more teeth and recording a third color component image data on the monochrome sensor array while the monochrome sensor array in the intra-oral camera is moving or still.

12. The method of claim 11, where said combining each set of the at least three monochromatic shading images comprises combining the recorded first, second, and third color component image data for each image pixel with color calibration data to generate a set of color values for said each image pixel, where said color calibration data is a prescribed color linear calibration matrix.

13. The method of claim 12, further comprising projecting a structured pattern at a first power level and projecting the light of at least one spectral band of the first spectral band, of the second spectral band, or of the third spectral band, at a second power level that differs from the first power level.

14. The method of claim 13, wherein projecting the structured pattern comprises projecting polarized light of the first spectral band onto the one or more teeth or wherein projecting light of the first spectral band onto the one or more teeth and recording first color component image data comprises projecting non-polarized light.

15. The method of claim 1, where the rendering comprises displaying at least a portion of the generated color texture 3-D surface contour image of the one or more teeth.

16. The method of claim 1, further comprising blending color values in the 2-D color shading images corresponding to each texture fragment of the plurality of texture fragments.

17. The method of claim 16, further comprising calculating color difference along all edges of each texture fragment of the plurality of texture fragments as a boundary condition and calculating an interpolated color difference for all pixels within each texture fragment of the plurality of texture fragments, and applying the interpolated color difference to pixels within each texture fragment of the plurality of texture fragments as a blended version of an original color shading image.

18. A method for rendering a 3-D surface contour color image of a tooth, the method executed at least in part on a computer system and comprising:
    obtaining a 3-D mesh representing a 3-D surface contour image of the tooth as a plurality of polygonal faces according to image data recorded from a plurality of views of the tooth;
    identifying a contour image view pose for rendering the 3-D surface contour image using the 3-D mesh;
    obtaining a set having a plurality of 2-D color shading images, wherein said each 2-D color shading image of said plurality of color shading images has a corresponding 2-D view pose and is formed by combining a first monochromatic image having illumination of a first spectral band, a second monochromatic image having illumination of a second spectral band, and a third monochromatic image having illumination of a third spectral band;
    wherein the first monochromatic image, the second monochromatic image, and the third monochromatic image for each 2-D color shading image in the set are acquired at a same corresponding 2-D view pose and acquired on a monochromatic sensor array, and where the first spectral band, the second spectral band, and the third spectral band are substantially non-overlapping; and
    rendering the 3-D surface contour color image according to an association that relates selected polygonal faces of the plurality of polygonal faces of the 3-D mesh at the contour image view pose to one 2-D color shading image of the set of 2-D color shading images.

19. The method of claim 18, wherein rendering the 3-D surface contour image further comprises, for each polygonal face of the 3-D mesh, mapping a portion of the 2-D color shading image to a corresponding polygonal face of the plurality of polygonal faces that is defined by mapping feature points that define the corresponding polygonal face of the plurality of polygonal faces in the 3-D mesh to corresponding pixels in the one 2-D color shading image of the set of the plurality of 2-D color shading images.

20. The method of claim 18, wherein first and second adjacent polygonal faces of the 3-D mesh are respectively associated with two different members of the set of 2-D color shading images.

* * * * *